(12) United States Patent
Wang et al.

(10) Patent No.: US 6,443,980 B1
(45) Date of Patent: Sep. 3, 2002

(54) END SLEEVE COATING FOR STENT DELIVERY

(75) Inventors: Lixiao Wang, Maple Grove; Dachuan Yang, Plymouth; The Thomas Trinh Tran, Coon Rapids; Fernando DiCaprio, Mendota Heights; Brett A. Williams, Lino Lakes, all of MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/697,194

(22) Filed: Oct. 26, 2000

Related U.S. Application Data

(63) Continuation-in-part of application No. 09/427,805, filed on Oct. 27, 1999, now Pat. No. 6,331,186, which is a continuation-in-part of application No. 09/273,520, filed on Mar. 22, 1999, now Pat. No. 6,221,097.

(51) Int. Cl.[7] .......................... A61F 2/02; A61M 25/00
(52) U.S. Cl. ..................................................... 623/1.11
(58) Field of Search ............................. 623/1.11, 1.12, 623/1.17, 1.23; 606/190, 194, 198

(56) References Cited

U.S. PATENT DOCUMENTS

| | | | |
|---|---|---|---|
| 3,574,673 A | 4/1971 | Schweiger | 117/132 |
| 3,892,314 A | 7/1975 | Semp | 206/363 |
| 3,977,982 A | 8/1976 | Hertl | 252/60 |
| 4,588,398 A | 5/1986 | Daugherty et al. | 604/265 |
| 4,773,902 A | 9/1988 | Lentz et al. | 604/265 |
| 4,904,433 A | 2/1990 | Williamitis | 264/130 |
| 4,950,227 A | 8/1990 | Savin et al. | 604/8 |

(List continued on next page.)

FOREIGN PATENT DOCUMENTS

| | | |
|---|---|---|
| EP | 0 442 657 A2 | 2/1990 |
| EP | 0 688 545 A1 | 6/1995 |
| EP | 0 682 145 A2 | 11/1995 |
| EP | 0 688 545 | 12/1995 |
| EP | 0 916 318 | 5/1999 |
| WO | 96/03092 A1 | 2/1996 |
| WO | 00/56248 | 9/2000 |
| WO | 01/34219 | 5/2001 |

OTHER PUBLICATIONS

U.S. patent application Ser. No. 09/273,520, Wang et al., filed Mar. 22, 1999.
U.S. patent application Ser. No. 09/427,805, Wang et al., filed Oct. 27, 1999.
U.S. patent application Ser. No. 09/549,286, Gerberding et al., filed Apr. 14, 2000.
U.S. patent application Ser. No. 09/552,807, Hanson, filed Apr. 20, 2000.
U.S. patent application Ser. No. 09/644,267, Dicaprio et al., Sep. 18, 2000.
U.S. patent application Ser. No. 09/664,268, Hanson, Sep. 18, 2000.
U.S. patent application Ser. No. 09/668,496, Yang, filed Sep. 22, 2000.

*Primary Examiner*—Cary E. O'Connor
(74) *Attorney, Agent, or Firm*—Vidas, Arrett & Steinkraus, P.A.

(57) ABSTRACT

A stent delivery system which utilizes a stent delivery catheter to deliver a stent into a body lumen. The stent delivery catheter being equipped with at least one stent retaining sleeve. The at least one stent retaining sleeve having an inside surface and an outside surface. The inside surface, outside surface, or both, having a coating which is lubricious.

27 Claims, 4 Drawing Sheets

U.S. PATENT DOCUMENTS

| | | | |
|---|---|---|---|
| 5,108,416 A | 4/1992 | Ryan et al. | 606/194 |
| 5,160,790 A | 11/1992 | Elton | 428/412 |
| 5,403,341 A | 4/1995 | Solar | |
| 5,409,495 A | 4/1995 | Osborn | 606/108 |
| 5,503,631 A | 4/1996 | Onishi et al. | 604/96 |
| 5,534,007 A | 7/1996 | St. Germain et al. | 606/108 |
| 5,556,414 A | 9/1996 | Turi | 606/198 |
| 5,634,928 A | 6/1997 | Fischell et al. | 606/108 |
| 5,690,644 A | 11/1997 | Yurek et al. | 606/108 |
| 5,693,014 A | 12/1997 | Abele et al. | 604/96 |
| 5,695,499 A | 12/1997 | Helgerson et al. | 606/108 |
| 5,702,418 A | 12/1997 | Ravenscroft | 606/198 |
| 5,746,745 A | 5/1998 | Abele et al. | 606/108 |
| 5,800,517 A | 9/1998 | Anderson et al. | 623/1 |
| 5,843,090 A | 12/1998 | Schuetz | 606/108 |
| 5,843,092 A | 12/1998 | Heller et al. | 606/108 |
| 5,843,158 A | 12/1998 | Lenker et al. | 623/1 |
| 5,911,711 A | 6/1999 | Pelkey | 604/265 |
| 5,944,726 A * | 8/1999 | Blaeser et al. | 606/108 |
| 5,951,569 A | 9/1999 | Tuckey et al. | 606/108 |
| 5,968,069 A | 10/1999 | Dusbabek et al. | 606/194 |
| 5,980,530 A | 11/1999 | Willard et al. | 606/108 |
| 5,980,533 A | 11/1999 | Holman | 606/108 |
| 6,010,480 A | 1/2000 | Abele et al. | 604/96 |
| 6,010,521 A | 1/2000 | Lee et al. | 606/194 |
| 6,015,398 A | 1/2000 | Arimatsu et al. | 604/272 |
| 6,046,143 A | 4/2000 | Khan et al. | 508/208 |
| 6,071,266 A | 6/2000 | Kelley | 604/265 |
| 6,160,032 A * | 12/2000 | Shah et al. | 523/112 |
| 6,183,505 B1 | 2/2001 | Mohn, Jr. et al. | 623/1.11 |

* cited by examiner

END SLEEVE COATING FOR STENT DELIVERY

CROSS-REFERENCE TO RELATED U.S. PATENT APPLICATIONS

This patent is a continuation-in-part of U.S. patent application Ser. No. 09/427,805 filed Oct. 27, 1999 now U.S. Pat. No. 6,331,186, and U.S. patent application Ser. No. 09/273,520 filed Mar. 22, 1999 now U.S. Pat. No. 6,221,097, incorporated by reference herein in their entirety.

BACKGROUND OF THE INVENTION

The patent relates to a delivery system in which a catheter carries on its distal end portion a stent which is held in place around the catheter prior to and during percutaneous delivery by means of one and preferably two end sleeves which have been coated with a lubricious material. The lubricious material is added to the sleeve material subsequent to extrusion of the sleeve material. The lubricious material increases the ease with which the stent may be deployed, and facilitates insertion of the catheter into a patients vasculature.

The stent may be self-expanding, such as a NITINOL shape memory stent, or it may be expandable by means of an expandable portion of the catheter, such as a balloon.

Stents and stent delivery systems are utilized in a number of medical procedures and situations, and as such their structure and function are well known. A stent is a generally cylindrical prosthesis introduced via a catheter into a lumen of a body vessel in a configuration having a generally reduced diameter and then expanded to the diameter of the vessel. In its expanded configuration, the stent supports and reinforces the vessel walls while maintaining the vessel in an open, unobstructed condition.

Both self-expanding and inflation expandable stents are well known and widely available in a variety of designs and configurations. Self-expanding stents must be maintained under a contained sheath or sleeve(s) in order to maintain their reduced diameter configuration during delivery of the stent to its deployment site. Inflation expandable stents are crimped to their reduced diameter about the delivery catheter, then maneuvered to the deployment site and expanded to the vessel diameter by fluid inflation of a balloon positioned between the stent and the delivery catheter. The present invention is particularly concerned with delivery and deployment of inflation expandable stents, although it is generally applicable to self-expanding stents when used with balloon catheters.

An example is the stent described in PCT Application NO. 960 3092 A1, published Feb. 8, 1996, the content of which is incorporated herein by reference.

In advancing an inflation expandable stent through a body vessel to the deployment site, there are a number of important considerations. The stent must be able to securely maintain its axial position on the delivery catheter without translocating proximally or distally, and more importantly, without becoming separated from the catheter. The stent, particularly any potentially sharp or jagged edges of its distal and proximal ends, must be protected to prevent edge dissection and prevent abrasion and/or reduce trauma of the vessel walls.

Inflation expandable stent delivery and deployment systems are known which utilize restraining means that overlie the stent during delivery. U.S. Pat. No. 4,950,227 to Savin et al., relates to an inflation expandable stent delivery system in which a sleeve overlaps the distal or proximal margin (or both) of the stent during delivery. During inflation of the stent at the deployment site, the stent margins are freed of the protective sleeve(s). U.S. Pat. No. 5,403,341 to Solar, relates to a stent delivery and deployment assembly which uses retaining sheaths positioned about opposite ends of the compressed stent. The retaining sheaths of Solar are adapted to tear under pressure as the stent is radially expanded, thus releasing the stent from engagement with the sheaths. U.S. Pat. No. 5,108,416 to Ryan et al., describes a stent introducer system which uses one or two flexible end caps and an annular socket surrounding the balloon to position the stent during introduction to the deployment site. The content of all of these patents is incorporated herein by reference.

This invention provides an improvement over the cited art, by selectively coating or otherwise lubricating the sleeve subsequent to its extrusion. This is in contrast to prior methods of lubricating the sleeve, such as by incorporating a lubricant additive within the polymeric composition of the sleeve, such as described in U.S. patent application Ser. No. 09/273,520, the entire contents of which is hereby incorporated by reference. In addition, the present invention avoids the use of collars, rings or other devices used to secure the sleeves to the catheter by bonding an end of a sleeve to the catheter directly.

SUMMARY OF THE INVENTION

The present invention relates to a stent delivery system comprising a stent delivery catheter which is equipped with at least one, and preferably two, stent retaining sleeves. The stent retaining sleeves are further characterized as having an inside surface and an outside surface, and a lubricious coating disposed on at least a portion of at least one of the inside and/or outside surfaces.

The lubricious coating may be hydrophilic or hydrophobic. In some particular embodiments, the outside surface is coated with a hydrophilic material. In other embodiments, the inside surface is coated with a hydrophobic material.

More particularly, in specific embodiments of the invention, the lubricious coating is either a hydrophobic or a hydrophilic gel-like material including hydrogels, and hydrophobic moisture curable silicones blended with a silicone oil or plasticizer. Hydrophilic silicone materials also find utility herein.

These gel-like materials are high molecular weight, viscous materials that have little tendency to migrate or wick from the surface to which they are applied. Applying such materials to the sleeve material right after extrusion also improves the adherence of the materials to the sleeve surface(s).

In other embodiments, a fluid and/or dry lubricant is coated onto the sleeve material after it has been extruded.

In yet another embodiment, the lubricious coating is a polyalkylene oxide, in particular, a polyethylene glycol.

The present invention further relates to a stent delivery system comprising a stent delivery catheter which is equipped with at least one, and preferably two, stent retaining sleeves. The stent retaining sleeve(s) are further characterized as having an inside surface and an outside surface, and the outside surface being at least partially coated with a hydrophilic lubricious coating.

BRIEF DESCRIPTION OF THE SEVERAL VIEWS OF THE DRAWINGS

A detailed description of the invention is hereafter described with specific reference being made to the drawings in which.

DETAILED DESCRIPTION OF THE INVENTION

Figure 1:
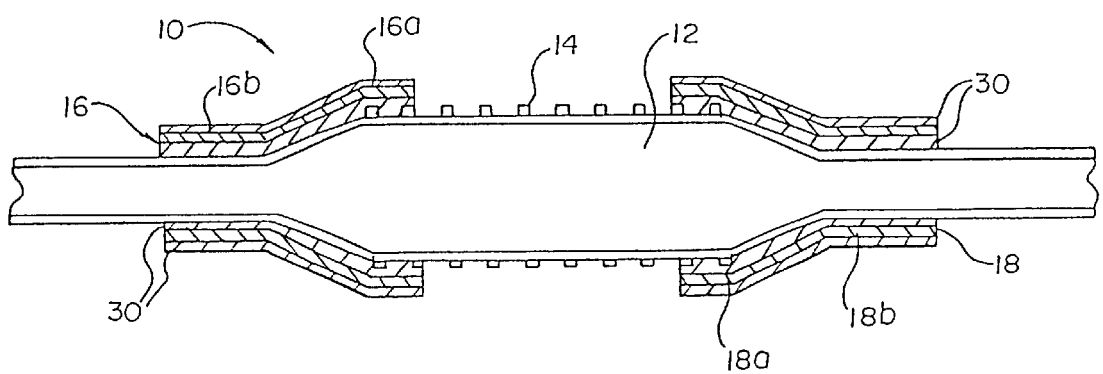
FIG. 1 is a schematic sectional side view of an embodiment of the inventive stent delivery system wherein the sleeves are coated with a lubricious gel on their inside and outside surfaces.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

FIG. 1 shows an embodiment of the present invention wherein a catheter generally designated 10 has an expandable portion or balloon 12. The expandable portion may be an inherent part of the catheter, as shown, or alternatively may be a separate balloon which is affixed to the catheter in any of the manners which may be known to one of ordinary skill in the art. Disposed about balloon 12 is a stent 14 as shown. Stent 14 may be any stent type capable of being delivered by a stent delivery catheter, such stents may be self-expanding or balloon expandable.

Attached to the catheter 10 are a pair of sleeves 16, 18. The sleeves each include a first portion 16a, 18a. When the balloon 12 is in the non-inflated state first sleeve portions 16a, 18a overlay the ends of balloon 12 as well as the ends of stent 14 as shown. Sleeves 16 and 18 also include respective second portions 16b and 18b. Regardless of the state of the balloon 12, non-inflated or inflated, second sleeve portions 16b, 18b are fixedly attached to catheter 10. The second sleeve portions may be attached to the catheter utilizing any method of attachment known. Such methods of attachment may include, but are not limited to: bonding or welding the sleeves to the catheter surface, applying an adhesive between the catheter and sleeve surface, or employing a mechanical attachment device such as a retaining ring or collar as is well known in the art. Preferably, the sleeves each have a thickness within the range of 0.0010 to 0.0060 in ches.

In the embodiment shown in FIG. 1, lubricious coating 30 is disposed on both the inner surface 17a, 19a and outer surface 17b, 19b of sleeves 16, 18. However, in other embodiments, the lubricious coating may be disposed about either the inner surface 17a, 19a or the outer surface 17b, 19b of sleeves 16, 18 consecutively, and is not disposed about both surfaces.

In some particular embodiments of the present invention, the lubricious coating 30 is preferably applied to the interior and/or exterior surfaces of the sleeves 16 and 18 after the sleeve material has been extruded. This is prior to construction of the stent delivery system.

Figure 2:
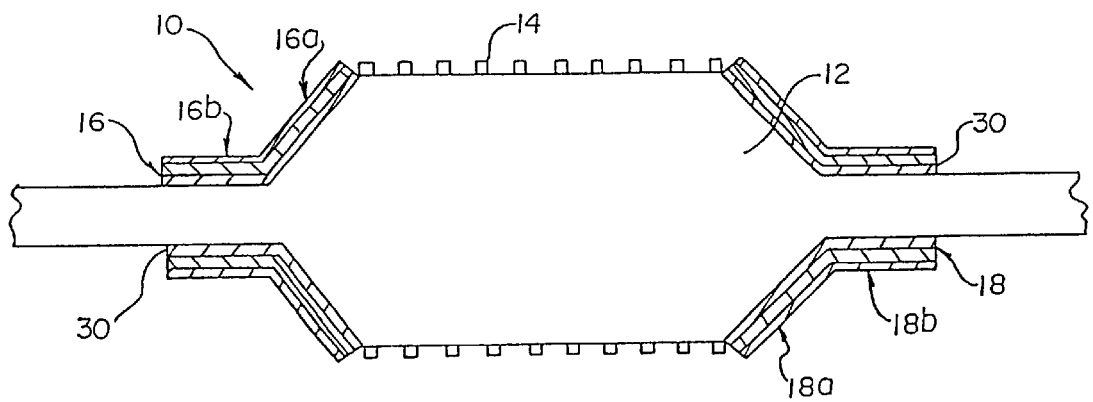
FIG. 2 is a similar view showing the embodiment of the stent delivery system shown in FIG. 1 when the balloon has been inflated to the inflated state.

A lubricious coating on the outside surfaces may provide improved trackability and movement of the catheter in a body lumen, while a lubricious coating on the inner surface facilitates deployment of the stent. Lubricious coating 30 facilitates retraction of the sleeves and thus assists in deployment of stent 14 by allowing the ends of balloon 12 and stent 14 to slide more readily away from the sleeves when balloon 12 is inflated, as seen in FIG. 2. Once the ends of stent 14 are no longer overlaid by sleeves 16 and 18 the stent is allowed to fully expand.

Figure 3:
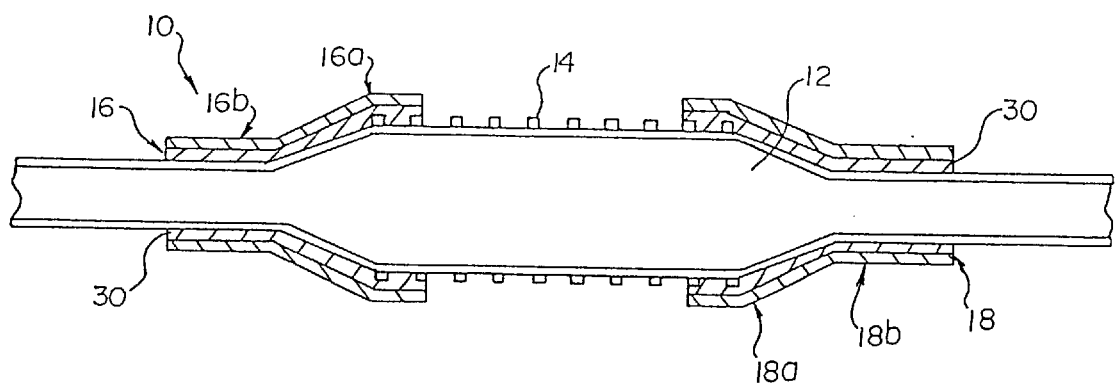
FIG. 3 is a similar view showing an embodiment of the stent delivery system wherein the sleeves are coated with lubricious gel on only their inside surfaces.

FIG. 3 illustrates an embodiment of the invention in which only the inner surfaces 17a, 19a of sleeves 16, 18 are coated.

Figure 4:
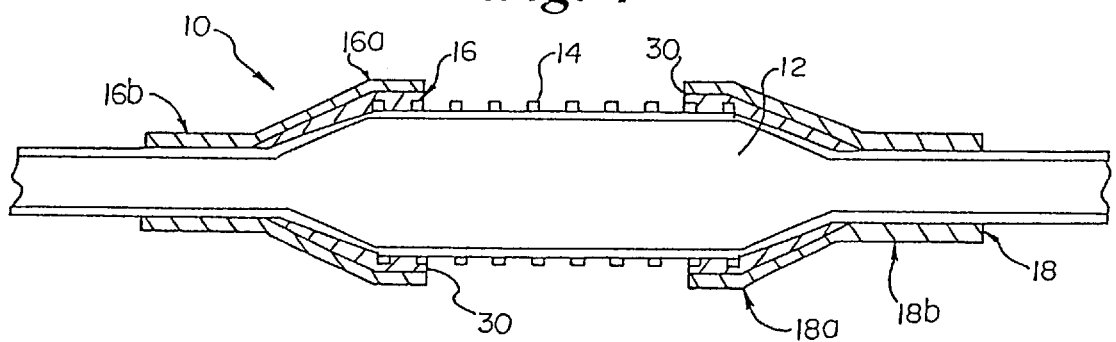
FIG. 4 is a similar view showing an embodiment of the stent delivery system wherein only a portion of the inside surface of the sleeves is coated with lubricious gel.

Because different lubricious coating types may have diverse characteristics, some lubricious coatings may interfere with the attachment of the sleeves to the catheter. In such an instance, it may be desirable or necessary to coat only specific portions of the sleeves. More specifically, in order to ensure proper securement of second sleeve portions 16b and 18b to catheter 10 it may be desirable or necessary to avoid coating the second sleeve portions, as shown in FIG. 4. However, the benefits provided by lubricious coating 30 are substantially maintained in this instance by coating only the inside surface of first sleeve portions 16a and 16b, thereby ensuring that the ends of the stent and balloon may be readily withdrawn from under the sleeves when the balloon is inflated.

Figure 5:
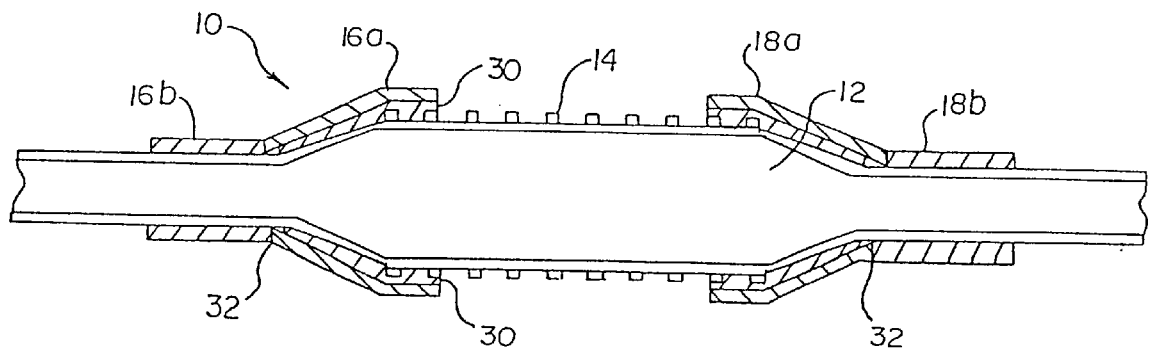
FIG. 5 is a similar view showing an embodiment of the stent delivery system wherein the sleeves are extruded from different polymer compositions which have then been bonded together.

Because of various manufacturing limitations inherent in the production of elastomeric polymer sleeves of the type described and preferably used herein, it is often more desirable to extrude and shape the polymer material into a tube which is to be used in the manufacture of the sleeve, then to separate the portion of the tube which will overlie the ends of the stent and balloon and separately coat these sections i.e., 16a and 18a. After the appropriate sections are coated they may be heat cured and then bonded, welded or otherwise attached to the uncoated sections 16b and 18b which will be connected to the catheter. The embodiment shown in FIG. 5 shows such the stent delivery system with such bonded sleeves. First sleeve sections 16a and 18a have lubricous coating 30 applied to their inside surfaces. They are then connected to the second sleeve sections 16b, 18b with a weld 32. Weld 32 may be a lap weld, a butt weld, an adhesive or any other means of connection which may be known to one of ordinary skill in the art.

Figure 6:
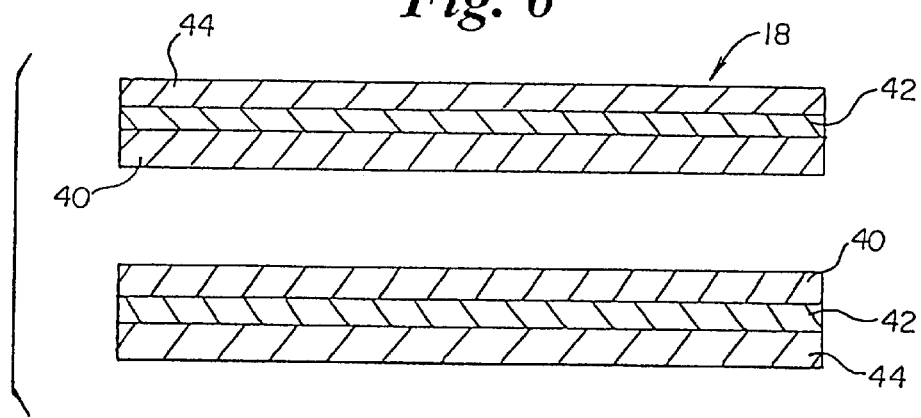
FIG. 6 is a similar view showing an embodiment of a stent delivery sleeve having a continuous tri-layer construction.
Figure 7:
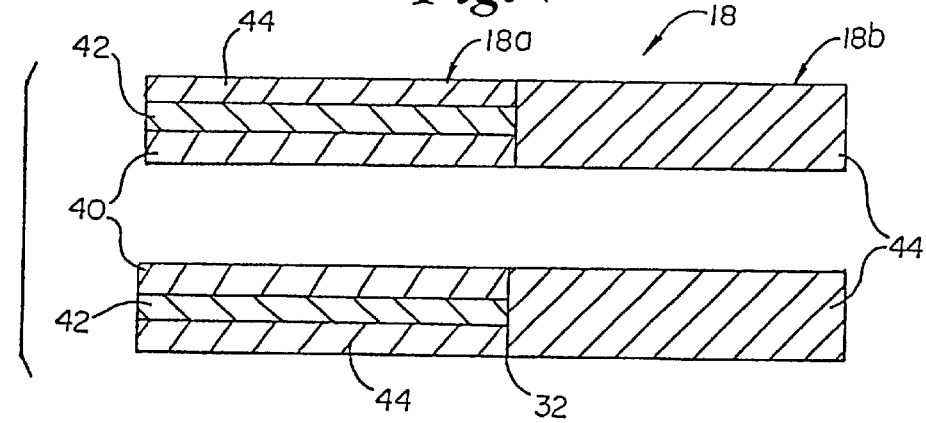
FIG. 7 is a similar view showing an embodiment of a stent delivery sleeve having a partial tri-layer construction.

Because stent retaining sleeves may be composed from materials which may be unsuitable for placing an effective layer of lubricious material upon, in another embodiment of the present invention the sleeves may have a tri-layer construction such as shown in FIGS. 6 and 7. Where the sleeves have a tri-layer construction the sleeves may be comprised of an inner layer 40 which is an inherently lubricous polymer.

In FIGS. 6 and 7, in order to show two potential embodiments of sleeves which may include the tri-layer construction described above, the sleeves are shown in an exaggerated scale. Furthermore, respective FIGS. 6 and 7 each show only a single sleeve 18, sleeve 16 is a left-handed mirror image of sleeve 18 as shown. In the embodiment shown in FIG. 6, inner layer 40 may extend through out the length of a sleeve 18 or in an alternative embodiment shown in FIG. 7, may be confined to only a portion of the sleeve such as the first sleeve portions 16a and 18a. Opposite the inner layer 40 is outer layer 44. Outer layer 44 is composed of any polymer material which can be used in any of the embodiments of the present invention already described herein, preferably having elastomer properties as well as heat shrinkable properties. The lubricious inner layer 40 and the outer polymer layer 44 are joined by an intermediate layer 42. The intermediate layer or third is composed of material which is characterized as being capable of bonding to the inner lubricous polymer material on one surface, and the outer sleeve polymer material on the other. Preferably, the intermediate layer is composed of PLEXAR® 380, thermoplastic polymers including polypropylene, polyurethane or other similar materials.

In the embodiment shown in FIG. 7, it may also be more desirable to bond first sleeve portion 18a, to the second sleeve portion 18b, with a weld 32 or other method of attachment as described as described in relation to FIG. 5 above.

Figure 8:
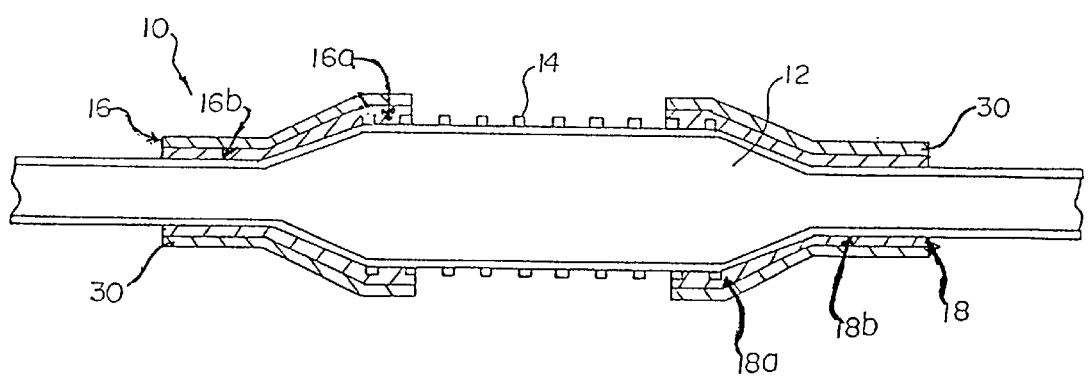
FIG. 8 is illustrative of an embodiment of the stent delivery system wherein the outer surface of the sleeves is coated with a lubricious coating material.

In yet another embodiment of the present invention, it may be desirable to coat only the outer surfaces of the sleeves, although as noted above, both the inner and outer surfaces may be coated, or the inner surface only may be coated as well. As shown in FIG. 8, only the outer surface 17b, 19b of sleeves 16 and 18 are coated with lubricious coating 30 to improve the lubricity.

The sleeves 16 and 18 are preferably coated without coating the stent or balloon structures themselves. The coating may be applied either by dipping or by brushing. Dipping, however, typically involves coating both the inner and outer surfaces of the sleeves 16 and 18 as shown in FIG. 1. The coating typically requires drying or curing time which time may be decreased by the addition of a heating source. Certain types of coatings may require moisture in order to crosslink or cure.

For illustrative purposes, lubricious coating 30 is shown in the various drawings with a highly exaggerated thickness. The coating thickness may vary from about 0.2 to about 20 $\mu$m, particularly for coating the outer surface 17b, 19b of sleeves 16, 18. However, it is preferable to the present invention that lubricious coating 30 is less than 0.0001 inches thick (2.54 $\mu$ or 2.54×10$_{-3}$ mm), particularly in the case where only the inner surfaces 17a, 19a of sleeves 16, 18 are coated. The lubricious coating may be comprised of either hydrophobic or hydrophilic lubricants.

In some preferred embodiments of the present invention, the lubricious coating 30 is a gel-like material. Some particularly useful materials in this category include those referred to as "hydrogels." These polymers are hydrophilic in nature and typically have the ability to dissolve or swell in an aqueous environment. These polymers are capable of manifesting lubricity while in a wet state, and when hydrated, exhibit low frictional forces in humoral fluids such as saliva, digestive fluids and blood, as well as in saline solution and water.

Such hydrogel compounds include polyethylene oxides (optionally linked to the substrate surface by interpenetrating network, IPN, with poly(meth)acrylate polymers or copolymers; copolymers of maleic anhydride; (meth) acrylamide polymers and copolymers; (meth)acrylic acid copolymers; poly(vinyl pyrrolidone) and blends or interpolymers with polyurethanes; and polysaccharides.

Other polymeric materials which hydrogels may comprise include polyalkylene glycols, alkoxy polyalkylene glycols, copolymers of methylvinyl ether and maleic acid, poly(N-alkylacrylamide), poly(acrylic acid), poly(vinyl alcohol), poly(ethyleneimine), polyamides, methyl cellulose, carboxymethyl cellulose, polyvinyl sulfonic acid, heparin, dextran, modified dextran and chondroitin sulphate.

In a specific embodiment, a hydrogel of polyethylene oxide may be captured in an interpenetrating crosslinked acrylic polymer network by polymerizing a mixture of an acrylic monomer composition comprising a monomer having plural (meth)acrylate groups and polyethylene oxide, thereby providing a hydrogel coating.

Examples of other types of crosslinkable hydrophilic lubricants useful herein include esterified polymers, salts, amides, anhydrides, halides, ethers, hydrolyzates, acetals, formals, alkylols, quaternary polymers, diazos, hydrazides, sulfonates, nitrates and ion complexes.

Examples of hydrophobic coatings useful to the present invention include applying a thin layer of silicone, functionalized silicone, or silanes that will hydrolyze to form a crosslinked silicone structure, or some mixture thereof.

Silicones or silicone blends may also form a gel-like material depending on the types used. For instance, using a blend of a hydrolyzable siloxane, such as an amino terminated siloxane, and a non-crosslinkable silicone oil, can result in a gel-like coating. The crosslinkable siloxane can crosslinks on the surface of the sleeves and the non-curing silicone then acts as a lubricant. The non-curing silicone plasticizes the crosslinked siloxane and may cause the crosslinked structure to swell, resulting in a gel-like composition wherein the non-curing silicone provides lubricity.

An example of such a blend of a crosslinkable siloxane with a non-curing silicone oil is a blend of Dow Corning DC-360, a non-curing polydimethylsiloxane (PDMS) and Silastic® MDX4-4159, an amino terminated polydimethyl siloxane also available from Dow Corning in Midland, Mich. and described in U.S. Pat. No. 4,904,433 and U.S. Pat. No. 3,574,673 both of which are incorporated by reference herein in their entirety. Another useful siloxane of this type is Silastic® MDX4-4210. This blend can be dissolved in solvent and then applied to the material to be coated out of solvent. For instance, 2% of the silicone blend can be dissolved in 98% heptane. The application of heat results in rapid evaporation of the solvent, and ambient moisture results in a structure crosslinked through —Si—O—Si— linkages. Sesame oil can also be used as a plasticizer.

Terminal groups that are activated by moisture and that will form a durable structure crosslinked through —Si—O—Si— linkages include, but are not limited to, $C_1$ to $C_{12}$ alkoxy groups, in particular the lower $C_1$ to $C_4$ alkoxy groups such as methoxy or ethoxy, $C_2$ to $C_4$ acryloxy, up to about $C_6$ (poly)alkoxyalkoxy, phenoxy, amine, oxime, halogen groups including chlorine, fluorine and bromine, and so forth. In particular emodiments of the present invention, hydrolyzable groups including the alkoxy, alkoxyalkoxy and the acryloxy groups are used.

Other examples of moisture crosslinkable silanes or siloxanes include, but are not limited to, 1-methoxy-3-(trimethylsiloxy)butadiene; methyltrimethoxysilane; triphenylsilanol; 1,1,3,3-tetramethyl-1,3-diethoxydisiloxane; triethylacetoxysilane; and so forth.

Using highly viscous gel-like coatings is preferable for use herein because the use of such materials decreases the tendency of the lubricious coating to be drawn, migrate, or "wick" over the various surfaces of the stent.

Wicking is undesirable because it may result in lubricant being introduced into the vessel wall of the patient when the stent is delivered into a body lumen, potentially leading to inflammation and restenosis. Wicking can also lead to more difficulty in securing the stent to the balloon prior to delivery the stent into the vessel. The affected stent causes increased crimping pressure which results in crimping processes which may be prone to more readily cause the stent to rupture the balloon. Therefore, the present stent deployment system has reduced parameters for crimping the stent to the balloon, which provides for a crimping process which is much more balloon friendly.

Dry lubricants also find utility in the present invention, and may used alone, or in combination with a fluid lubricant.

Examples of dry lubricants useful herein include those described as solid lamellar form lubricants such as graphite and modified tungsten disulfides such as those sold under the tradename of DICRONITE® available from Dicronite Dry Lube.

Another dry lubricant which may be applied using vapor deposition techniques is sold under the tradename of PARYLENE®. These materials are high molecular weight hydrocarbon materials available from Advanced Coating in Rancho Cucamonga, Calif. PARYLENE® materials are referred to as di-para-xylylene (dimers) materials and are available in several forms including the following:

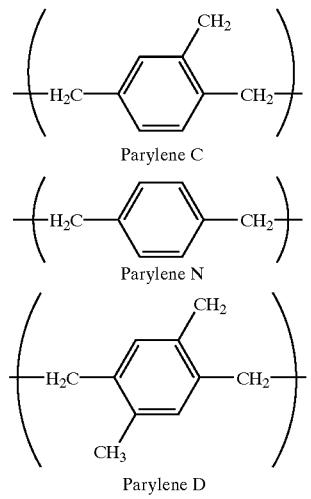

Examples of other hydrophilic coatings particularly useful herein include polyalkylene oxides (polyalkylene glycols) and alkoxy polyalkylene glycols including the high molecular weight polyethylene glycols sold under the tradename of CARBOWAX® and sold by Union Carbide in Danbury, Conn. Polyethylene Glycols are non-toxic, water-soluble polymers that are considered to be biodegradable. Polyethylene oxide/polypropylene oxide block copolymers and methoxypolyethylene oxides are also useful herein.

There are many examples of other hydrophilic coatings useful in the present invention including, but not limited to, synthetics such as the homopolymers and copolymers of (meth)acrylic acid including poly(acrylic acid), homopolymers and copolymers of maleic acid such as copolymers of methylvinyl ether and maleic acid, homopolymers and copolymers of maleic anhydride such as methyl vinyl ether-maleic anhydride copolymers such as Gantrez® AN 169 available from G.A.F. Corp. and poly(ethylene-maleic anhydride) sold by Aldrich Chemical Co., pyrrolidones such as poly(vinylpyrrolidone) homopolymers, copolymers of vinyl pyrrolidone, acryl amides including poly(N-alkylacrylamides), poly(vinyl alcohols), poly(carboxylic acids), poly(ethyleneimines), polyamides (e.g. water soluble nylons), polyvinylsulfonic acids, polyurethanes, and so forth.

Copolymers with vinyl groups, acrylic acid, methacrylic acid, fumaric acid, maleic acid, maleic anhydride, diene compounds, or other polymerizable ethylenically unsaturated compounds are another particular group of polymers which find utility herein. The acids may be optionally be neutralized.

Naturally occurring hydrophilic compounds also find utility herein and include methyl cellulose, carboxymethylcellulose, hydroxyethyl cellulose, hydroxypropyl cellulose, polyvinylsulfonic acid, heparin, dextran, modified dextran, chondroitin sulphate, lecithin, and so forth.

These hydrophilic polymers typically contain a hydrophilic group such as —OH, —CONH$_2$, —COOH, —NH$_2$, —COO—, —SO$_3$, —NR$_3^+$ where R is alkyl or hydrogen, and so forth.

Derivatives of any of these hydrophilic polymers may be utilized providing that enough of the basic structure of the polymers above that provides water sensitivity, solubility or dispersibility is retained allowing the polymer to uptake enough water to swell or partially dissolve enough upon exposure to moisture to provide lubricity in such a way to reduce frictional forces between the surface it is coated on and another surface such as tissue, metal or polymeric surfaces. Water insoluble derivatives may be employed as long as they have the freedom in the molecular chain and can be hydrated. Examples include esterified polymers, salts, amides, anhydrides, halides, ethers, hydrolyzates, acetals, formals, alkylols, quaternary polymers, diazos, hydrazides, sulfonates, nitrates, and ion complexes which are obtained by condensation, addition, substitution, oxidation, or reduction reactions of the above-mentioned water soluble polymers. Also used are polymers crosslinked with substances having more than one reactive functional group such as diazonium, azide, isocyanate, acid chloride, acid anhydride, imino carbonate, amino, carboxyl, epoxy, hydroxyl, and aldehyde groups.

The hydrophilic polymers of the present invention may be utilized in any combination to more narrowly tailor the resultant composition to the application. Some of the hydrophilic polymers of the present invention exhibit less flexibility than others.

The present invention also contemplates the use of slip additives or antiblock agents to the hydrophilic coatings of the present invention, particularly in those embodiments in which the outer surface of the sleeves are coated with a lubricious hydrophilic coating.

The coating compositions of the present invention may be coated out of a solvent or a cosolvent mixture using any conventional coating techniques such as dipping, spraying, brushing, and so forth.

While these hydrophilic coatings have been discussed in relation to an embodiment directed more toward coating the outer surface of sleeves, they may also be used to coat the inner surface of the sleeves, or both.

Useful solvents include alcohols, aliphatic hydrocarbons, aromatic hydrocarbons, chlorinated solvents, esters, glycols, glycol ethers, ketones, and so forth. Polar solvents include alcohols, glycols, water and so forth. Specific examples include ethanol, methanol, isopropanol, stearyl alcohol, ethylene glycol, propylene glycol, glycerin, water and so forth. Non-polar solvents include aliphatic hydrocarbons such as heptane and hexane; aromatic hydrocarbons such as toluene and xylene; chlorinated hydrocarbons such as perchloroethylene, methylene chloride, chloroform, carbon tetrachloride, 1,1,1-trichloroethane; fluorocarbons; mineral spirits and so forth.

In the case of hydrophilic coatings, the preferable solvents are more polar and preferably include the alcohols such as isopropyl alcohol or isopropanol and water and mixtures thereof.

This completes the description of the preferred and alternate embodiments of the invention. Those skilled in the art may recognize other equivalents to the specific embodiment described herein which equivalents are intended to be encompassed by the claims attached hereto.

What is claimed is:

1. A stent delivery system comprising a stent delivery catheter which is equipped with at least one stent retaining sleeve, the at least one stent retaining sleeve being further characterized as having an inside surface and an outside surface, said sleeve having a lubricious coating on at least a portion of at least one of said inside surface and said outside surface said lubricious coating comprising at least one selected from the group consisting of hydrogels, homopolymers and copolymers of polyalkylene oxides, homopolymers or copolymers of at least one polymerizable ethylenically unsaturated compound, and mixtures thereof.

2. The stent delivery system of claim 1 wherein said hydrogel is a hydrogel of polyethylene oxide captured in an interpenetrating crosslinked acrylic polymer network by polymerizing a mixture of an acrylic monomer composition comprising a monomer having plural (meth)acrylate groups and polyethylene oxide, thereby providing a hydrogel coating.

3. The stent delivery system of claim 1 wherein said lubricious coating comprises at least one homopolymer or copolymer of polyalkylene oxide.

4. The stent delivery system of claim 3 wherein said lubricious coating is a polyalkylene oxide homopolymer which is a polyethylene glycol.

5. The stent delivery system of claim 1 wherein said lubricious coating comprises at least one polycarboxylic acid selected from maleic acid, fumaric acid and (meth)acrylic acid.

6. The stent delivery system of claim 1 wherein said lubricious coating comprises at least one copolymer of maleic anhydride.

7. The stent delivery system of claim 6 wherein said maleic anhydride copolymer is selected from poly(ethylene-maleic anhydride) copolymers and maleic anhydride-methyl vinyl ether copolymers.

8. A stent delivery system comprising a stent delivery catheter which is equipped with at least one stent retaining sleeve, the at least one stent retaining sleeve being further characterized as having an inside surface and an outside surface, said sleeve having a lubricious coating comprising at least one polymer which moisture cures.

9. A stent delivery system comprising a stent delivery catheter which is equipped with at least one stent retaining sleeve, the at least one stent retaining sleeve being further characterized as having an inside surface and an outside surface, said sleeve having a lubricious coating on at least a portion of at least one of said inside surface and said outside surface said lubricious coating comprising at least one hydrolyzable siloxane and at least one plasticizer.

10. The stent delivery system of claim 9 wherein said at least one hydrolyzable siloxane is an amino terminated hydrolyzable siloxane.

11. The stent delivery system of claim 9 wherein said at least one hydrolyzable siloxane comprises terminal groups selected from $C_1$ to $C_{12}$ alkoxy, $C_2$ to $C_4$ acryloxy, up to about $C_6$ (poly)alkoxyalkoxy, phenoxy, amine, oxime, chlorine, fluorine and bromine.

12. The stent delivery system of claim 9 wherein said at least one plasticizer is a silicone oil.

13. A stent delivery system comprising a stent delivery catheter which is equipped with at least one stent retaining sleeve, the at least one stent retaining sleeve being further characterized as having an inside surface and an outside surface, said sleeve having a lubricious coating on at least a portion of at least one of said inside surface and said outside surface wherein said lubricious coating comprises at least one hydrolyzable siloxane and nonhydrolyzable siloxane.

14. The stent delievery system of claim 13 wherein said lubricious coating comprises at least one amino terminated hydrolyzable polydimethylsiloxane and at least one nonhydrolyzable polydimethylsiloxane.

15. A stent delivery system comprising a stent delivery catheter which is equipped with at least one stent retaining sleeve, the at least one stent retaining sleeve being further characterized as having an inside surface and an outside surface, said sleeve having a lubricious coating on at least a portion of at least one of said inside surface and said outside surface said lubricious coating comprises at least one dry lubricant.

16. The stent delivery system of claim 15 wherein said dry lubricant is a hydrocarbon material.

17. The stent delivery system of claim 15 wherein said dry lubricant is a solid lamellar form lubricant.

18. A stent delivery system comprising a stent delivery catheter which is equipped with at least one stent retaining sleeve, the at least one stent retaining sleeve being further characterized as having an inside surface and an outside surface, the inside surface being at least partially coated with a hydrophobic material and the outside surface being at least partially coated with a hydrophilic lubricious coating.

19. The stent delivery system of claim 18 wherein at least one stent retaining sleeve is comprised of an extruded polymeric material.

20. The stent delivery system of claim 18 wherein said lubricious coating is selected from hydrogels, homopolymers and copolymers of polyalkylene oxides, homopolymers or copolymers of at least one polymerizable ethylenically unsaturated compound, and mixtures thereof.

21. The stent delivery system of claim 20 wherein said hydrogel is a hydrogel of polyethylene oxide captured in an interpenetrating crosslinked acrylic polymer network by polymerizing a mixture of an acrylic monomer composition comprising a monomer having plural (meth)acrylate groups and polyethylene oxide, thereby providing a hydrogel coating.

22. The stent delivery system of claim 20 wherein said lubricious coating comprises at least one homopolymer or copolymer of polyalkylene oxide.

23. The stent delivery system of claim 22 wherein said lubricious coating is a polyalkylene oxide homopolymer which is a polyethylene glycol.

24. The stent delivery system of claim 20 wherein said lubricious coating comprises at least one polycarboxylic acid selected from maleic acid, fumaric acid, (meth)acrylic acid, and mixtures thereof.

25. The stent delivery system of claim 18 wherein said lubricious coating comprises at least one copolymer of maleic anhydride.

26. The stent delivery system of claim 25 wherein said maleic anhydride copolymer is selected from poly(ethylene-maleic anhydride) copolymers and maleic anhydride-methyl vinyl ether copolymers.

27. A stent delivery system comprising a stent delivery catheter which is equipped with at least one stent retaining sleeve, the at least one stent retaining sleeve being further characterized as having an inside surface and an outside surface, said sleeve having a hydrophilic lubricious coating on at least a portion of said inside surface, said lubricious coating comprising at least one hydrophilic lubricant selected from the group consisting of esterified polymers, salts, amides, anhydrides, halides, ethers, hydrolyzates, acetals, formals, alkylols, quaternary polymers, diazos, hydrazides, sulfonates, nitrates, ion complexes and mixtures thereof.

* * * * *